(12) United States Patent
Edwards

(10) Patent No.: US 9,889,268 B2
(45) Date of Patent: Feb. 13, 2018

(54) ON-SITE MEDICAL GAS PRODUCTION PLANT AND ASSOCIATED OPERATING METHOD

(71) Applicant: L'Air Liquide, Societe Anonyme Pour l'Etude et l'Exploitation des Procedes Georges Claude, Paris (FR)

(72) Inventor: Paul Edwards, Mississauga (CA)

(73) Assignee: L'Air Liquide, SociétéAnonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/596,253

(22) Filed: May 16, 2017

(65) Prior Publication Data
US 2017/0252530 A1    Sep. 7, 2017

Related U.S. Application Data

(62) Division of application No. 14/489,506, filed on Sep. 18, 2014, now Pat. No. 9,682,210.

(30) Foreign Application Priority Data

Sep. 27, 2013 (CA) ..................................... 2829065

(51) Int. Cl.
    *B01D 53/02*    (2006.01)
    *A61M 16/10*    (2006.01)
    (Continued)

(52) U.S. Cl.
    CPC ...... *A61M 16/1005* (2014.02); *A61M 16/201* (2014.02); *B01D 53/0454* (2013.01);
    (Continued)

(58) Field of Classification Search
    CPC ............ A61M 16/1005; A61M 16/201; A61M 2205/3327; B01D 2253/10;
    (Continued)

(56) References Cited

U.S. PATENT DOCUMENTS

| 4,983,190 A | 1/1991 | Barkley et al. |
| 5,071,453 A | 12/1991 | Hradek |

(Continued)

FOREIGN PATENT DOCUMENTS

| EP | 0 297 542 | 1/1989 |
| EP | 0 537 612 | 4/1993 |

(Continued)

OTHER PUBLICATIONS

European Search Report and Written Opinion for corresponding EP 12155272, dated May 31, 2012.

*Primary Examiner* — Christopher P Jones
(74) *Attorney, Agent, or Firm* — Allen E. White

(57) ABSTRACT

The invention relates to an on-site medical gas production plant (100) comprising a unit (50) for purifying gas, such as air, a first compartment (A) for storing purified gas, and a main gas line (10) fluidically connecting the gas purification unit (50) to the said first storage compartment (A). It furthermore comprises a three-way actuated valve (VA) arranged on the main gas line (10) upstream of the first storage compartment (A), and furthermore connected to the atmosphere (at 12) via a vent line (11), as well as an operating device (4) which controls at least the three-way actuated valve (VA), and at least a first gas analysis device (D1) of which a first measurement line (29) is fluidically connected (at 28) to the main line (10), upstream of the three-way actuated valve (VA), and which is electrically connected to the said operating device (4).

11 Claims, 2 Drawing Sheets

(51) Int. Cl.
    *A61M 16/20*     (2006.01)
    *B01D 53/30*     (2006.01)
    *G01N 27/416*     (2006.01)
    *G01N 33/00*     (2006.01)
    *B01D 53/04*     (2006.01)
    *B01D 53/053*     (2006.01)
    *B01D 53/047*     (2006.01)

(52) U.S. Cl.
CPC ......... *B01D 53/30* (2013.01); *G01N 27/4162* (2013.01); *G01N 33/0031* (2013.01); *A61M 2205/3327* (2013.01); *B01D 53/047* (2013.01); *B01D 53/0462* (2013.01); *B01D 53/053* (2013.01); *B01D 2253/10* (2013.01); *B01D 2257/302* (2013.01); *B01D 2257/404* (2013.01); *B01D 2257/502* (2013.01); *B01D 2257/504* (2013.01); *B01D 2257/702* (2013.01); *B01D 2257/80* (2013.01); *B01D 2258/06* (2013.01); *B01D 2259/402* (2013.01); *B01D 2259/4533* (2013.01); *Y02C 10/08* (2013.01)

(58) Field of Classification Search
CPC ........ B01D 2257/302; B01D 2257/404; B01D 2257/502; B01D 2257/504; B01D 2257/702; B01D 2257/80; B01D 2258/06; B01D 2259/402; B01D 2259/4533; B01D 53/0454; B01D 53/0462; B01D 53/047; B01D 53/053; B01D 53/30; G01N 27/4162; G01N 33/0031; Y02C 10/08
See application file for complete search history.

(56) References Cited

U.S. PATENT DOCUMENTS

| | | |
|---|---|---|
| 5,199,423 A | 4/1993 | Harral et al. |
| 5,915,834 A | 6/1999 | McCulloh |
| 6,125,655 A | 10/2000 | Millet et al. |
| 6,270,557 B1 | 8/2001 | Millet et al. |
| 6,394,089 B1 | 5/2002 | Cantrill |
| 6,478,857 B2 | 11/2002 | Czabala |
| 7,204,249 B1 | 4/2007 | Richey |
| 2004/0079359 A1 | 4/2004 | Aylsworth et al. |
| 2007/0214960 A1 | 9/2007 | Aylsworth et al. |
| 2011/0226126 A1 | 9/2011 | Grahl |
| 2013/0205999 A1 | 8/2013 | Sommier et al. |

FOREIGN PATENT DOCUMENTS

| | | |
|---|---|---|
| EP | 0 716 274 | 6/1996 |
| EP | 0 718 024 | 6/1996 |
| EP | 0 864 818 | 9/1998 |
| EP | 0 922 482 | 6/1999 |
| EP | 0 930 089 | 7/1999 |
| FR | 2 658 155 | 8/1991 |
| GB | 1 551 348 | 8/1979 |

ON-SITE MEDICAL GAS PRODUCTION PLANT AND ASSOCIATED OPERATING METHOD

CROSS REFERENCE TO RELATED APPLICATIONS

This application is a divisional of U.S. patent application Ser. No. 14/489,506 filed Sep. 18, 2014 which claims the benefit of priority under 35 U.S.C. §119 (a) and (b) to Canadian Patent Application No. 2,829,065 filed Sep. 27, 2013, the entire contents of which are incorporated herein by reference.

BACKGROUND

The invention relates to a plant for medical air production on-site, that is to say in a hospital building or the like, employing a three-way solenoid valve adapted to discharge product gas contaminated by impurities to the atmosphere via a purge line connected to one of the ports of the solenoid valve, and to a method for controlling or operating such a plant.

The medical air used in hospitals, clinics, treatment centres, emergency or incident units, or the like, for patients' respiration is a medicament whose composition is specified by the European Pharmacopoeia.

More precisely, medical air is ambient air compressed to a pressure above atmospheric pressure, typically several bars, or to tens or even hundreds of bars and containing (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water and at most 0.1 $mg/m^3$ oil; the oil vapours possibly present essentially come from the compression of the air.

It should be noted that, other than oxygen, the components mentioned above (i.e. COx, NOx, water, or oil etc.) are in fact impurities whose presence is tolerated within the limits of the Pharmacopoeia but which ideally are not present therein.

Medical air furthermore contains nitrogen, and may also contain other compounds, such as argon.

Currently, medical air is delivered to hospitals or the like in three forms, namely, depending on the case:
  direct delivery in the form of compressed air, for example at an absolute pressure of from 200 to 300 bar, in cylinders, that is to say bottles or canisters of gas, or containers comprising a plurality of bottles;
  production on-site by mixing oxygen and nitrogen so as to create nitrogen/oxygen mixtures, and
  direct production on-site from ambient air treated, in particular, by compressors and filtration/purification systems.

Of these, the production of air directly on-site by compressors and filtration systems is the most widespread solution. Such a method is described, for example, in the document EP-A-864818.

The ambient air is taken in and compressed by compressors to a pressure range extending from 1 bar to 80 bar relative. This compressed air is then filtered, that is to say purified, by means of one or more treatment steps, for example by a set of filters and/or by employing a pressure swing adsorption method (PSA).

The medical air produced in this way may be stored in one or more intermediate buffer compartments, then sent through the network of pipes which passes through the hospital building in order to provision the treatment rooms, bedrooms or the like with medical air. It is quite clearly possible, and even indispensable in certain cases, to carry out intermediate expansion of the gas, for example in order to change from a pressure of about 10 bar in the storage compartment to a pressure of 5 or 8 bar in the network.

In general, any break in medical air provision is overcome by using medical air taken from a reserve or backup source in which the air is kept in gaseous form.

The other medical gases used in hospitals or treatment centres, such as oxygen, are also delivered in a similar way to the air. The compositions of these other gases are also specified by the European or US Pharmacopoeia.

Thus, oxygen may also be produced on-site by a PSA method by using specific adsorbents, such as lithium-exchanged zeolites X, making it possible to retain the nitrogen contained in the air and thus produce gaseous oxygen having a purity typically greater than 90%, or even 93% by volume, as is known from the document EP-A-297542.

However, the methods for producing medical air or other medical gases used on-site (also referred to as on-site methods) present certain drawbacks.

First, these methods do not permit easy monitoring of the reliability of the manufacturing process.

Thus, when an on-site medical air production unit is operating autonomously, the manufacturing process is not overseen continuously and the interventions on the plant take place on the basis of planning, that is to say preventive maintenance, or when an error or a problem arises in the plant, that is to say curative maintenance.

These interventions are therefore carried out independently of the status of the plant and its reliability, which is not optimal because they are carried out either too soon, and therefore without actual need, or too late, and therefore with an impact on the production process and possibly on the final product.

Next, pollutant blockages in the main pipe occur when the gas produced is not compliant. This is because in existing plants, the control solenoid valve is a so called "2-way" solenoid valve which is arranged on the main line.

Although it makes it possible to stop possible pollution upstream of the valve, this pollution nevertheless remains blocked in the main line and necessitates a total purge of the system upstream of the valve. This is not ideal because it entails a shutdown of the gas production and manual intervention.

Furthermore, in the event of short-term breaks in the air provision due, for example, to temporary contamination at the inlet, the backup source is resorted to directly. However, this poses a problem because the backup volume is limited and therefore, if the frequency of the breaks in provision is high, there is then a risk of draining the backup source. In other words, it would be highly beneficial to be able to avoid this drawback by reducing the extent to which the backup source is used, so as to increase its autonomy over time.

Lastly, the air produced by the current methods and plants is in general neither analyzed nor validated in pharmaceutical terms, which may raise obvious problems of compliance and quality. Furthermore, when it is analyzed, in the event of "noncompliance" this usually leads either to immediate interruption of the production and changeover to a backup source air, which may entail overuse of the backup air liable to cause a possible total break in the air provision, or to continuous provision of noncompliant air and parallel triggering of an alarm in order to warn the user, who then needs to intervene manually. It will be understood that these solutions are not ideal either.

In summary, there is currently no method of validating air produced on-site which makes it possible to ensure that the air produced is in fact compliant with the required specifications and which makes it possible to ensure effective and reliable provision of medical air.

In other words, the problem which arises is to provide a plant for continuous on-site production of a medicament gas, particular medical air, in accordance with good manufacturing practice (GMP) and a method for controlling or operating such a plant, which permit in particular:

- supervision of the reliability of the manufacturing process with rapid detection of any anomaly,
- monitoring of the various production steps and in particular the final production with, for each step, the possibility of a purge thus making it possible to stop any contamination or noncompliance of the gas produced, in particular medical air, and/or
- the use of the backup sources to be reduced to a minimal level.

SUMMARY

The solution of the invention is a plant for on-site production of medical gas, in particular medical-quality air, comprising:

- a gas purification unit adapted to produce a purified gas from a supply gas,
- a first compartment for storing purified gas, and
- a main gas line fluidically connecting the gas purification unit to the said first storage compartment so as to supply the said first storage compartment with purified gas coming from the gas purification unit,
- characterized in that it furthermore comprises:
- a three-way actuated valve arranged on the main gas line between the gas purification unit and the said first storage compartment, and furthermore connected to the atmosphere via a vent line,
- an operating device which controls at least one three-way actuated valve,
- at least a first gas analysis device of which a first measurement line is fluidically connected to the main line, upstream of the three-way actuated valve,
- and which is electrically connected to the said operating device, and in which the operating device is designed and adapted to act on the three-way actuated valve in response to a signal received from the gas analysis device, so as to allow the gas present in the main pipe to pass to the vent line when the signal received from the gas analysis device corresponds to a "contamination" signal of the main pipe, and simultaneously to prevent any gas being sent to the said first storage compartment.

Depending on the case, the plant of the invention may comprise one or more of the following technical characteristics:

- the gas compression unit supplies the gas purification unit with a gas to be purified, compressed to a pressure higher than 1 bar absolute.
- the gas compression unit supplies the gas purification unit with compressed ambient air.
- the gas compression unit comprises at least one screw, piston, scroll or diaphragm compressor.
- the gas compression unit comprises a plurality of compressors, in particular arranged in parallel.
- the gas purification unit comprises at least one adsorber, each containing at least one bed of at least one adsorbent material, preferably at least 2 adsorbers arranged in parallel.
- the gas purification unit comprises at least one adsorber operating in a cycle of the PSA type.
- the gas purification unit comprises at least two adsorbers operating alternately, and the operating device is designed and adapted to act on the gas purification unit and/or the gas compression unit so as to stop any production of gas by the adsorber which was in operation at the time when the gas analysis device transmitted the "contamination" signal of the main pipe to the operating device.
- the "contamination" signal corresponds to a given level of at least one impurity, in particular one or more impurities selected from water vapour, or oil vapours, SOx, COx and/or NOx.
- the "contamination" signal corresponds to a preset threshold level, for example corresponding to a maximum level set by the United States or European Pharmacopoeia as regards the aforementioned impurities (i.e. water and oil vapour, SOx, COx and/or NOx) or a maximum limit value lower than the said corrected maximum values (for example 80% or 90% of the maximum value in the Pharmacopoeia), which makes it possible to ensure an operational safety margin.
- the operating device is designed and adapted to act on the (two or three-way) actuated valve(s) in response to a signal received from the gas analysis device, so as to stop any gas present in the main pipe from passing to the vent line when the signal received from the gas analysis device corresponds to a "compliant gas" signal of the main pipe, and simultaneously to allow gas to be sent to the said first storage compartment.
- the gas purification unit furthermore comprises one or more filters.
- the gas purification unit, in particular the adsorbers, makes it possible to eliminate all or some of the impurities which are possibly present in the ambient air to be purified or which have been introduced therein during the compression, in particular water vapour, oil vapours, SOx, COx and/or NOx, so as to produce a medical gas compliant with the Pharmacopoeia, in particular medical air compliant with the European Pharmacopoeia. The adsorbers may include desiccants and/or deliquescent dryers. Alternatives to adsorber based systems are refrigerant dryers or membrane dryers. Generally any suitable device for dehumidifying the air is compatible with the device and system described herein.
- the valve is a 3-way actuated valve, of which one of the ports is fluidically connected via a vent line to the atmosphere and the other two ports are fluidically connected to the main line.
- the valve is an actuated valve controlled by an operating unit, preferably the operating unit electrically connected to the three-way actuated valve.
- The gas compression unit comprises one (or more) gas inlets supplied with atmospheric air.
- the main line connects the first compartment for storing purified gas to at least one gas consumer site, preferably a network of pipes in a hospital building
- the main gas line comprises a second compartment for storing purified gas, located between the first storage compartment and the said at least one gas consumer site. The first and second compartments are therefore arranged in series on the main line.
- the main gas line branches downstream of the first storage compartment into a secondary line fluidically connected upstream to the said main line and downstream to at least one gas consumer site, that is to say directly or indirectly, for example by being connected to the main gas line, the said secondary gas line comprising a third compartment for storing purified gas. The first and third compartments are therefore also arranged in series, whereas the second and third compartments are arranged in parallel on the main line and the secondary line, respectively.

it furthermore comprises a backup line fluidically connecting a backup source, such as a reserve or store of medical air, to the said at least one gas consumer site, either directly or indirectly by being connected to the main gas line or the said secondary line.

it furthermore comprises at least 2-way actuated valves are typically 2-way actuated valves, arranged on the main line or the secondary line, with a first actuated valve arranged between the first compartment and the second compartment for storing purified gas, and a second actuated valve arranged between the first compartment and the third compartment for storing purified gas, it furthermore comprises at least two-way actuated valves, arranged on the main line and the secondary line, with a third actuated valve arranged downstream of the second compartment and/or a fourth actuated valve arranged downstream of the third compartment, it furthermore comprises a first purge line, fluidically connected upstream to the main line and downstream to the vent line, the first purge line preferably being fluidically connected to the main line downstream of the second compartment.

it furthermore comprises a second purge line fluidically connected upstream to the secondary line and downstream to the vent line, the second purge line preferably being fluidically connected to the secondary line downstream of the third compartment.

the first purge line comprises a fifth actuated valve and/or the second purge line comprises a sixth actuated valve.

it comprises at least a first gas analysis device, the first measurement line of which is fluidically connected to the main line, upstream of the three-way actuated valve, it comprises a second gas analysis device, of which at least one second measurement line is fluidically connected to the main line and/or to the secondary line.

the second measurement line comprises a seventh and/or an eighth actuated valve.

the operating unit furthermore controls the gas purification unit, the gas compression unit, one or more of the actuated valves and the gas analysis device or devices.

it comprises one or more nonreturn valves arranged on all or some of the pipes or lines conveying the gas.

The invention also relates to a method for operating an on-site medical gas production plant, in particular a plant according to the invention as described above, comprising the steps of:

a) producing a purified gas from a supply gas, in particular atmospheric air compressed to a pressure greater than atmospheric pressure (i.e. >1 atm), b) transporting the purified gas obtained in step a) by means of a main gas pipe, c) storing at least a part of the purified gas in a first compartment the storing the gas supplied by the gas pipe, characterized in that it furthermore comprises the steps of:

d) determining in the main gas pipe, upstream of the first storage compartment, an impurity level of at least one given impurity in the gas produced in step a), and e) controlling a three-way actuated valve arranged on the main gas line upstream of the first storage compartment, and furthermore connected to the atmosphere via a vent line, so as to divert the gas present in the main pipe, upstream of the three-way actuated valve, to the vent line when the impurity level measured in step d) is greater than or equal to a preset threshold level.

Depending on the case, the method of the invention may comprise one or more of the following technical characteristics:

in step e), the gas present in the main pipe, upstream of the three-way actuated valve, is diverted to the vent line and gas is simultaneously stopped from being sent to the first storage compartment, when the impurity level measured in step d) is greater than or equal to a preset threshold level.

in step a), a purified gas is produced from a supply gas treated in a gas purification unit comprising at least two adsorbers operating alternately, and when an impurity level greater than or equal to a preset threshold level is determined in the gas produced by one of the said adsorbers, the production of the gas by the said adsorber is stopped and the production of gas by the other or another of the said adsorbers is started.

gaseous flushing of the main pipe part containing an impurity level greater than or equal to the preset threshold level with purified gas is carried out and the gas flow thus generated is discharged to the atmosphere via the vent line.

the gas to be purified is ambient air and the purified gas is medical air or medical oxygen, that is to say with the specifications of the European Pharmacopoeia, as explained above.

the impurity or impurities are selected from NOx, SOx, COx, water vapour and hydrocarbon vapours, in particular oil vapours.

the medical air produced contains (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water, at most 0.1 mg/m$^3$ oil, and nitrogen.

in step d), a gas analysis device is used in order to determine the impurity level in the main gas pipe.

in step e), an operating device, such as a programmable automaton, is used in order to control the three-way actuated valve, the said operating device acting in response to the measurements taken by the gas analysis device.

BRIEF DESCRIPTION OF THE DRAWING

For a further understanding of the nature and objects for the present invention, reference should be made to the following detailed description, taken in conjunction with the accompanying drawing, in which like elements are given the same or analogous reference numbers and wherein.

DESCRIPTION OF PREFERRED
EMBODIMENTS

The present invention will now be described in more detail with reference to the appended FIGS. 1 and 2, which represent the block diagram of an embodiment of a plant 100 for on-site production of medical gases, controlled by the operating method according to the invention, which plant 100 is connected to the network of pipes 30 of a hospital building or the like.

The gas produced here is medical air, that is to say purified air satisfying the specifications of the European Pharmacopoeia mentioned above. Nevertheless, such a plant 100 may be used for manufacturing other medical gases, for example medical oxygen from ambient air.

Figure 1:
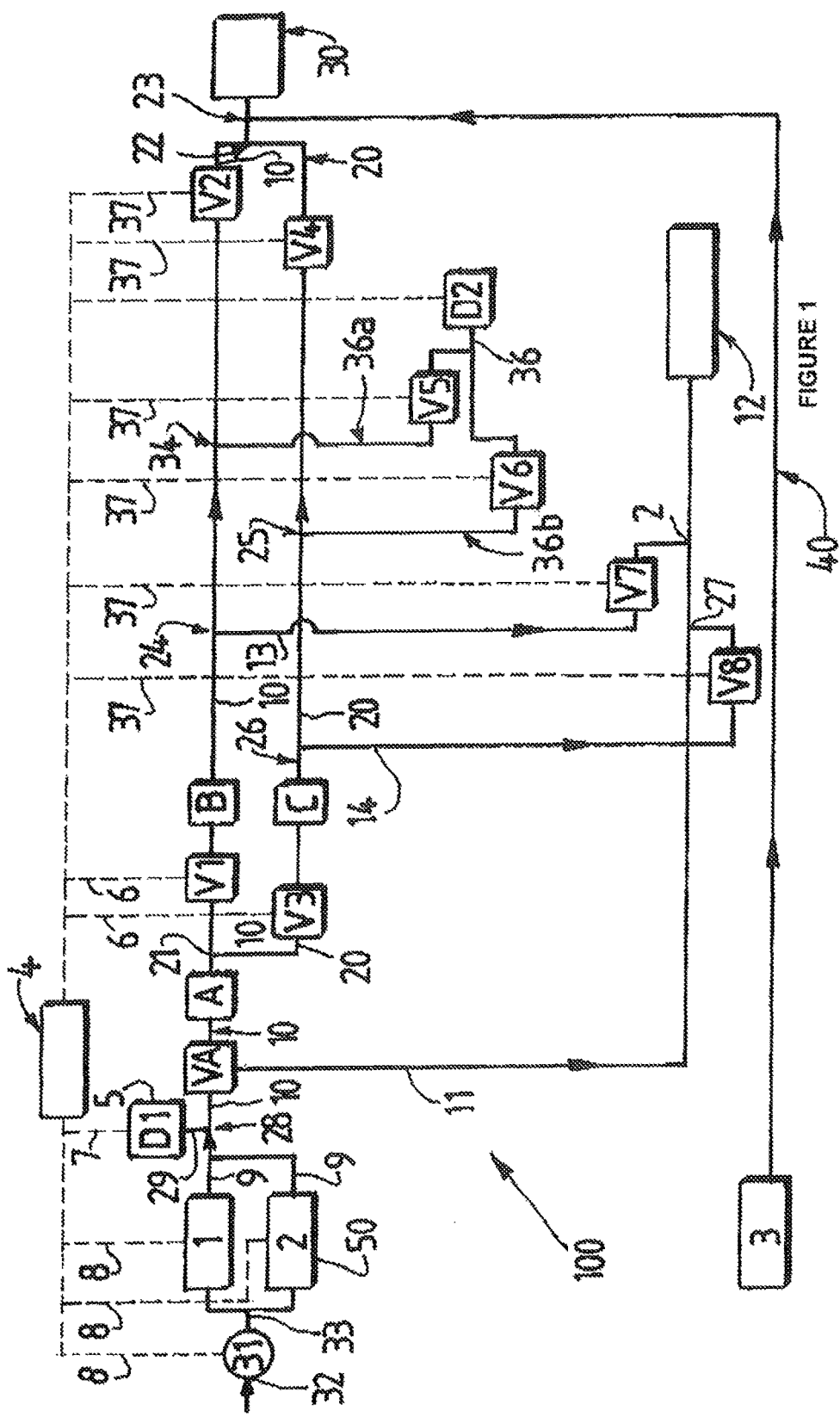
FIG. 1, which represents the block diagram of an embodiment of a plant 100 for on-site production of medical gases, controlled by the operating method according to the invention, which plant 100 is connected to the network of pipes 30 of a hospital building.

More precisely, in the embodiment illustrated in FIG. 1, the on-site medical air production plant 100 comprises a gas purification unit 50 supplied by a gas compression unit 31, that is to say one or more air compressors taking in ambient air at atmospheric pressure (i.e. 1 atm) through their supply inlet 32 and delivering compressed air at a pressure higher than atmospheric pressure, for example at a pressure of between 1 bar and 80 bar absolute. This compressor or these compressors 31 may be one or more screw, piston, scroll or diaphragm compressors.

The compressed air supplies the gas purification unit 50, which here comprises two adsorbers 1, 2 operating in parallel according to cycles of the PSA type (Pressure Swing Adsorption) or TSA type (Temperature Swing Adsorption), that is to say one is in production phase while the other is in regeneration phase, and vice versa. Typically, the duration of a production cycle is between 1 and 30 minutes, approximately, preferably from less than 10 to 15 minutes.

These adsorbers each contain at least one bed of at least one adsorbent material, for example adsorbent materials such as zeolites, aluminas, active carbon, silica gel or any other molecular sieve capable of stopping the impurities present in ambient air.

Depending on the embodiment in question, the gas purification unit 50 may also comprise a single adsorber or more than 2 adsorbers 1, 2, for example at least 3 adsorbers.

These types of adsorbers 1, 2 and PSA or TSA cycle are well known and, in this regard, reference may furthermore be made for example to the documents EP-A-716274, EP-A-718024, EP-A-922482, GB-A-1551348, EP-A-930089.

In all cases, the adsorbers 1, 2 make it possible to eliminate all or some of the impurities which are possibly present in the ambient air to be purified or which have been introduced therein during the compression (at 31), in particular water vapour, oil vapours, SOx, COx and/or NOx, so as to produce a medical gas compliant with the Pharmacopoeia, in particular medical air compliant with the European Pharmacopoeia.

Next, the purified air (or any other medical gas) produced by the gas purification unit 50 is recovered in outlet conduits 9 which supply a main line 10 conveying gas, that is to say a pipe or a tube delivering gas, which is adapted and designed to convey the purified air produced in this way to a first storage compartment A, that is defined as a buffer gas volume container such as a vessel, tank or discrete section of pipe in which the purified medical air can be stored and/or homogenized before being sent to one or more consumer sites 30, such as a network of gas pipes passing through a hospital building in order to convey the medical air to the various rooms in which it is to be used, such as treatment rooms, emergency rooms, recovery rooms, bedrooms or any other any other location.

Preferably the storage compartment A is in unidirectional fluid communication with the gas purification unit 50 via main line 10 such that gas entering the storage compartment A cannot return upstream toward the gas purification unit 50.

The main gas line 10 therefore fluidically connects the outlet (or outlets) 9 of the gas purification unit 50 to the said first storage compartment A so as to supply it with purified air coming from the two adsorbers 1, 2 of the gas purification unit 50.

The operation of the compressor or the compressors 31 and the purification cycles taking place in the gas purification unit 50 are controlled and monitored by an operating device 4, for example a programmable automaton or the like, connected to the gas purification unit 50 by electrical connections 8, such as electrical cables.

It should, however, be noted that communication between the various elements and devices of the plant, in particular with the automaton 4, could in general also take place via wireless links, for example via one or more wireless transmitter devices or systems such as radiofrequency (RF), Bluetooth, Zigbee, wifi, GSM or GPRS, and one or more receiver antennas for carrying out wireless transmissions of data adapted to the type of transmitter used.

Preferably, the automaton 4 or the like is programmed according to the requirements of the hospital site in question and can be reprogrammed if the requirements of the site change, for example.

In order to regulate and monitor the conveyance of gas in the main gas line 10, an actuated valve VA is arranged on the said main line 10 between the gas purification unit 50 and the first storage compartment A. The actuated valve VA is also controlled by the operating device 4 via an electrical connection 5, such as an electrical cable.

According to one preferred embodiment shown in FIG. 1, the valve VA is a three-way actuated valve such as a solenoid valve, one of the ports of which is fluidically connected via a vent line 11 to the ambient atmosphere (at 12) where there is preferably a device for venting to the atmosphere, such as a vent valve (not represented), and the other two ports of which are fluidically connected to the main line 10.

The air produced by the gas purification unit 50 therefore passes through two of the ports of the actuated valve VA, that is to say the first and second ports of the actuated valve VA, when it passes normally through the said actuated valve VA in the direction of the buffer compartment A where the purified gas can be stored.

Conversely, in the event of contamination of the line 10 upstream of the valve VA, this pollution can be expelled easily and effectively from the contaminated conduit portion of the main line 10, without the need for a total purge of the system upstream of the valve VA.

This is done conventionally by flushing the conduit portion polluted by impurities with pure air produced by the gas purification unit 50. The gas flow entraining the impurities is then discharged via the third port of the actuated valve VA to the atmosphere, through the vent line 11 to the ambient atmosphere. In other words, the air produced by the gas purification unit 1, 2 will then entrain the pollutants with it and these will be disposed of to the atmosphere (at 12).

The 3-way actuated valve VA therefore makes it possible not only to block any possible pollution on the main line 10 in order to confine it upstream of the actuated valve VA, but also subsequently to discharge this pollution of the main line 10 to the outside (at 12) and thus to purge the main line 10 upstream of the valve VA.

This solution makes it possible to avoid shutting down the production process entirely and resorting to the backup 3, that is to say a reserve of pure gas, in the event of temporary pollution of the air taken in or created by the production line.

Furthermore, the first buffer compartment A makes it possible to take over the delivery of the purified gas, such as medical air, when the valve VA is in the vent position, that is to say when a purge of the line 10 is ongoing, so as here again to reduce the frequency of use of the backup source 3.

The first compartment A also makes it possible to protect the production unit 50 from consumption peaks, that is to say peaks in demand from the consumer sites 30, and to homogenize the air produced by the production unit.

The monitoring of the composition of the gas produced, such as purified air, delivered by the production unit 50 is carried out by means of a first gas analysis device D1, such as an analysis cabinet or any other suitable gas analyzer, the measurement line 29 of which is connected fluidically (at 28) to the main line 10, upstream of the 3-way actuated valve VA.

This gas analysis device D1 is connected to the operating device 4 via an electrical connection 7, such as an electrical cable or the like, so as to transmit measurement signals and optionally other information thereto.

As a function of the signals received, the operating device 4 can retroact on the 3-way actuated valve VA and preferably the other elements of the plant, such as production unit 50, compressor 31, etc., in order to trigger a purge of the line 10 when pollution is detected.

More precisely, in order to evaluate the reliability of the method and of the production plant, the quality of the air produced is analyzed using the analysis cabinet D1, in particular the levels of $O_2$, $H_2O$, $CO_2$ and oil vapour. Complementary monitoring variables (for example temperature, pressure, vibrations, etc.) are furthermore collected from the plant.

The analysis results as well as the monitoring variables may also then be optionally processed by the operating device 4, such as an automaton, on the basis of statistical process control (SPC) in order to define the reliability of the production process.

The processing of the data is carried out for each of the production lines, that is to say for each of the adsorbers 1, 2 of the production unit 50 as well as the compressors 31, on the basis of conventional control elements, such as aptitude indicators of the production process, control chart of the variables, average, control limits, trend analysis of the variables, etc.

On the basis of the results and the predefined parameters, it is then possible to determine whether or not the manufacturing process is reliable.

Thus, when the operating device 4 determines that the level of one or more impurities in the main gas pipe 10, in particular upstream of the first storage compartment A, is greater than or equal to a preset threshold level, for example the maximum values set by the European Pharmacopoeia as regards the level of water vapour, or oil vapours, SOx, COx and/or NOx, the said operating device 4 controls the three-way actuated valve VA so as to divert the gas present in the main pipe 10, in particular the gas present upstream of the three-way actuated valve VA, to the vent line 11 and thus purge the main line 10 of the impure, that is to say non-compliant, gas contained therein.

In this case, i.e. when the manufacturing process is not reliable, or no longer reliable, the production line in question, that is to say the adsorbers 1 or 2 and the associated compressor 31, is shut down and the second line takes over for producing purified air, while the other line is regenerated, reinitialized and/or undergoes a maintenance operation.

In other words, in the event of excessive impurity levels, the gas present in the main pipe 10 is diverted to the vent line 11 and gas is simultaneously stopped being sent to the first storage compartment A.

At this time, the production of the gas by the adsorber 1 or 2 in question is stopped and production of gas by the other adsorber 1 or 2, respectively, of the production unit 50 is started.

This gas produced by the other adsorber will then be used to carry out gaseous flushing of the part of the main pipe 10 containing the impurity level greater than or equal to the preset threshold level then will subsequently be discharged to the atmosphere as a result of the gas flow thus generated, via the vent line 11.

When the pipe 10 has been purged and the impurity level has returned to normal, the operating device 4 will control the 3-way actuated valve VA in order to stop the purge and allow gas again to be sent to the compartments A, B and/or C located downstream.

The gas produced in this way is then subjected to monitoring as before.

In the event of unreliability of the second line as well, the system then switches to the backup source 3. Specifically, the plant also comprises a backup line 40 fluidically connecting a backup source 3, such as a backup reservoir containing medical air, to the gas consumer sites 30, directly or indirectly, that is to say by being connected at 23 to the main gas line 10 or to a secondary line 20.

The secondary line 20 is in fact another gas line arranged in parallel with the main line 10 and used as an alternative passage for the gas coming from the compartment A, for example, and/or from the production unit 50, when the main line 10 is out of use, for example contaminated and/or undergoing a maintenance operation.

In other words, the main gas line 10 branches (at 21) downstream of the first compartment A into a secondary line 20. The latter 20 is therefore fluidically connected on its upstream side (at 21) to the said main line 10 and, by its downstream end, to at least one gas consumer site (30), directly or indirectly, that is to say by being connected (at 22) to the main gas line 10.

Furthermore line 10 also comprises a second buffer compartment B for storing purified gas, located between the first compartment A and the gas consumer site or sites, such as a network of pipes 30 of a hospital building, and the secondary line 20 in turn comprises a third compartment C for storing purified gas.

The compartments B, C are used to supply the consumer site or sites 30 with respiratory gas. In fact, the compartments B and C are used to provide medical air in alternation, that is to say while one compartment (for example B) is being filled or analyzed for compliance, the second (respectively C) delivers the gas to the hospital network 30, or vice versa.

In general, maintenance of the plant 100 is triggered by the automaton 4 on an anticipatory basis when the production parameters of one or both production units 1, 2 reach a predetermined threshold.

It will furthermore be noted that 2-way actuated valves are arranged on the main line 10 and the secondary line 20. More precisely, a first actuated valve V1 is arranged between the first compartment A and the second compartment B, and a second actuated valve V3 is arranged between the first compartment A and the third compartment C for storing purified gas.

Furthermore, a third actuated valve V2 is arranged downstream of the second compartment B and a fourth actuated valve V4 is arranged downstream of the third compartment C. These 2-way actuated valves are controlled by the operating device 4 via electrical connections 6, 37, such as cables or the like, and make it possible to control the passage of the gas through the lines 10 and 20 and therefore to divide the pipes 10, 20 into well-determined sections, and also to manage and/or operate the gas inlets and/or outlets of the compartments B and C.

The plant 100 furthermore comprises a first purge line 13 fluidically connected by its upstream end 24 to the main line 10, preferably downstream of the second compartment B, and by its downstream end 25 to the vent line 11, as well as a second purge line 14 fluidically connected by its upstream end 26 to the secondary line 20, preferably downstream of the third compartment C, and by its downstream end 27 to the vent line 11.

The first purge line 13 comprises a fifth actuated valve V7 and the second purge line 14 comprises a sixth actuated valve V8 used to control the passage of the gas to the vent line 11. The operating device 4 also controls the actuated valves V7, V8 via electrical connections 37.

These purge lines 13, 14 make it possible to purge the portions of lines 10, 20 as well as the compartments B and C, respectively, located upstream of the actuated valves V2 and V4, respectively.

A second gas analysis device D2, such as an analysis cabinet or the like, is provided and includes at least one second measurement line 36, branching into two subsections 36a, 36b, which is fluidically connected (at 34, 35) to the main line 10 and to the secondary line 20, in particular by means of the subsections 36a, 36b. Preferably, the second measurement line 36, 36a, 36b comprises a seventh V5 and/or an eighth V6 actuated valve.

This second gas analysis device D2 makes it possible to determine the composition of the gas circulating in the main 10 and secondary 20 lines, downstream of the compartments B, C, that is to say it makes it possible to analyze discontinuously the gas taken from the compartments B and C. As before, this second gas analysis device D2 cooperates with the operating device 4, which itself controls the actuated valves V5, V6 via electrical connections 37.

The electrical supply of the plant 100 is carried out conventionally by current from the mains, for example at a voltage of between 1 and 600 V, typically 24 V, 230 V or 400 V.

If need be, measurement means (not shown) may be provided in order to determine the pressure of the medical air contained in the compartments A, B, C for storage and homogenization of the gas and optionally retroact via the operating device 4 on the compression unit 31 and/or the production unit 50 so as to regulate the production of the gas, such as air, by taking into account the pressure (or pressures) thus measured. For example, the operating means 4 may be programmed in order to cause shutdown of the flow source 31 and/or triggering of an audio and/or visual alarm, when a pressure sensor arranged at the buffer compartment A detects a pressure or a pressure difference greater than or, conversely, less than a preset threshold value. This type of pressure regulation is well known and will not be described in detail here.

Furthermore, in order to ensure even more effective purification of the air taken in by the compressor 31, one (or more) mechanical filtration devices (not represented in detail) may be provided, arranged at one or more sites between the air source 31 and the hospital network 30. For example, the compression unit may comprise one or more filters at the inlet 32 and/or outlet 33 in order to retain the dust contained in the ambient air and the condensates due to the compression, for example cyclone filters or separators, micron filters or the like.

Figure 2:
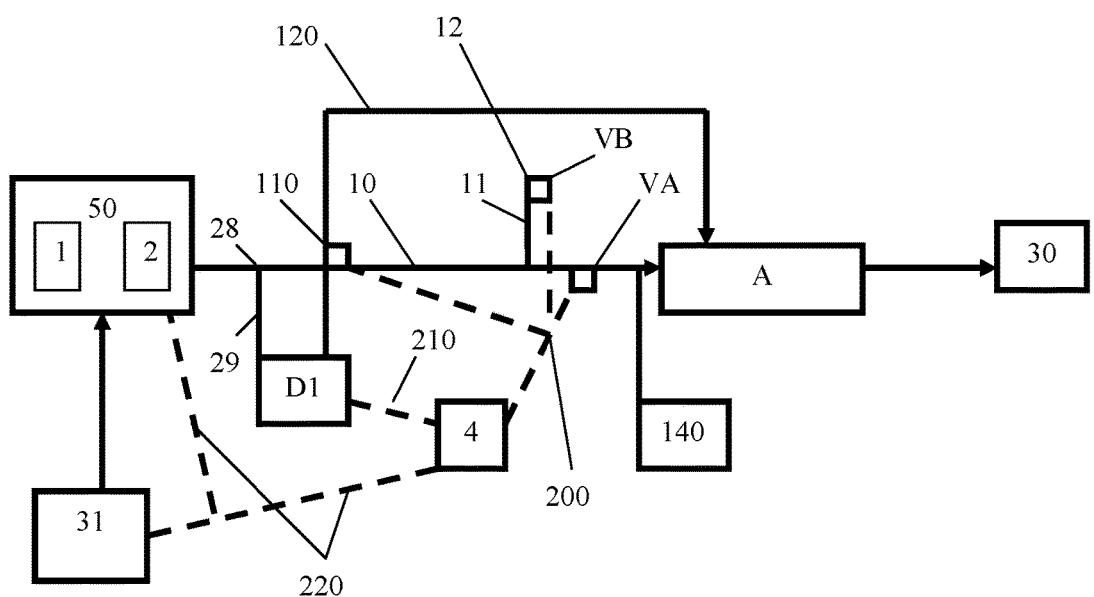
FIG. 2 illustrates and alternative arrangement of the invention having a single storage compartment A.

FIG. 2 illustrates and alternative arrangement of the invention having a single storage compartment A. The basic elements are the same as FIG. 1, namely the medical air production unit 50 fed by compressor 31 directing medical via main line 10 to a point of use 30 such as a hospital piping network. Storage compartment A in this example is a discrete section of pipe which is fluidically isolated from the preceding main line 10 such as by a one way check valve. In FIG. 2, each valve VA, VB and 110 may all be two way actuated valves under a common operating device 4 control 200 or one or more may be also, or exclusively manually operated. In one preferred embodiment, VA and VB are under operating device 4 control 200, but bypass valve 110 is a manual only valve. FIG. 2's design includes a backup medical air supply 140 which may be a tank or cylinder of medical air.

Medical air production unit 50 may, instead of being the air purification systems of FIGS. 1 and 2, be a synthetic air production system wherein oxygen and nitrogen gases are blended to form a respiratory gas substitute for air (synthetic air). The nitrogen and oxygen can be medical grade gases or can be purified to medical grade standards pre- or post-blending using an air purification system such as those described in FIGS. 1 and 2. The nitrogen and oxygen sources may be for example bulk storage tanks of cryogenic liquids that are vaporized and temperature adjusted pre- or post-blending. Other sources of gases for the synthetic air could include direct pipelines from an Air Separation plant or other means for storing or delivering the nitrogen and oxygen to the medical air production unit 50.

In general, the plant 100 of the invention for production of medical air on-site, that is to say in a hospital building or the like, therefore employs a three-way actuated valve adapted to discharge product gas contaminated by impurities to the atmosphere via a purge line connected to one of the ports of the actuated valve VA, in response to detection of the said contamination by an analysis device D1 cooperating with the operating device 4.

The medical air production plant 100 of the invention may be used directly on the site where the gas is used, that is to say directly in a hospital building or the like. It may therefore be installed directly in a room of the hospital building or outside the said building or in containers, and connected to the network 30 of pipes conveying the gas inside the building.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method for operating an on-site medical gas production plant (100), the plant comprising:
   a synthetic air production unit (50) configured to produce a mixture comprising nitrogen and oxygen which is medically suitable for respiration by patients in place of or in addition to air,
   a first compartment (A) for storing the purified gas, and
   a main gas line (10) fluidically connecting the synthetic air production unit (50) to the first storage compartment (A) so as to supply the said first storage compartment (A) with the synthetic air coming from the synthetic air production unit (50),
   wherein the main gas line furthermore comprises:
   an actuated valve (VA) arranged on the main gas line (10) between the synthetic air production unit (50) and the first storage compartment (A), and furthermore connected to the atmosphere (at 12) via a vent line (11),
   an operating device (4) which controls the at least one actuated valve (VA),
   at least a first gas analysis device (D1) of which a first measurement line (29) is fluidically connected (at 28) to the main line (10), upstream of the actuated valve (VA), and which is electrically connected to the operating device (4),
   and in which the operating device (4) is designed and adapted to act on the actuated valve (VA) in response to a signal received from the gas analysis device (D1), so as to divert a gas present in the main pipe (10) to pass to the vent line (11) when the signal received from the gas analysis device (D1) corresponds to a contamination signal based on an analysis of the gas in the main pipe (10), and simultaneously to prevent the gas present in the main pipe (10) from being sent to the said first storage compartment (A);
   the method comprising the steps of:
   a) producing a synthetic air comprising nitrogen and oxygen which is medically suitable for respiration by patients in place of or in addition to air,
   b) transporting the synthetic air obtained in step a) in a main gas pipe (10),
   c) storing at least a part of the synthetic air in a first compartment (A) for storing gas supplied by the main gas pipe (10),
   d) determining in the main gas pipe (10), upstream of the first storage compartment (A), an impurity level of at least one given impurity in the synthetic air produced in step a) based on the signal received from the gas analysis device (D1) corresponding to the contamination signal, and
   e) controlling an actuated valve (VA) arranged on the main gas line (10) upstream of the first storage compartment (A), and furthermore connected to the atmosphere (at 12) via a vent line (11), so as to divert the synthetic air present in the main pipe (10), upstream of the actuated valve (VA), to the vent line (11) when the impurity level measured in step d) is greater than or equal to a preset threshold level,
   wherein the contamination signal from the gas analysis device (D1) corresponds to a measurement for the level of NOx, SOx, COx, water vapour, hydrocarbon vapours, carbon monoxide, carbon dioxide, nitric oxide, nitrogen dioxide, sulphur dioxide, and combinations thereof.

2. The method according to claim 1, wherein in step e), the synthetic air present in the main pipe (10), upstream of the actuated valve (VA), is diverted to the vent line (11) and synthetic air is simultaneously stopped from being sent to the first storage compartment (A), when the impurity level measured in step d) is greater than or equal to a preset threshold level.

3. The method according to claim 2, wherein:
   in step a), the synthetic air production unit (50) comprises at least two adsorbers (1, 2) operating alternately, and
   when an impurity level greater than or equal to a preset threshold level is determined in the gas produced by one of the adsorbers, the production of the gas by the adsorber is stopped and the production of purified gas by another of the adsorber(s) is started.

4. The method according to claim 2, wherein a gaseous flushing step of the main pipe (10) containing an impurity level greater than or equal to the preset threshold level with synthetic air is carried out and the gas flow thus generated is discharged to the atmosphere via the vent line (11).

5. The method of claim 1, wherein the nitrogen and/or oxygen are from a less pure supply gas source to be purified by the synthetic air production unit (50) to yield a synthetic air that qualifies as is a medical air or a medical oxygen gas.

6. The method of claim 5, wherein the synthetic medical air meets the following criteria:
   19.5% to 23.5% oxygen, with predominant balance nitrogen
   Carbon monoxide: <10 ppm
   Carbon dioxide: <500 ppm
   Nitrogen dioxide: <2.5 ppm
   Nitric oxide: <2.5 ppm
   Sulfur dioxide: <5 ppm.

7. The method of claim 1, wherein the impurity or impurities are selected from NOx, SOx, COx, water vapour, hydrocarbon vapours, or combinations thereof.

8. The method of claim 5, wherein the medical air produced contains (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water, at most 0.1 mg/m$^3$ oil, and nitrogen.

9. The method of claim 5, wherein in step d), a gas analysis device (D1) determines the impurity level in the gas in the main gas pipe (10).

10. The method of claim 9, wherein in step e), an operating device (4) controls the actuated valve (VA), the operating device (4) acting in response to the measurements taken by the gas analysis device (D1).

11. The method of claim 10, wherein the operating device (4) monitors the signal received (210) from the gas analysis device (D1) during a first defined period of a purge operation to determine if the contamination signal persists for longer than a specified period of time and wherein, if the contamination signal persists for less than the specified period, the operating device (4) closes a vent line (11) actuated valve (VB) to end the purge operation and reopens the main line (10) actuated valve (VA) to resume delivery of gas from the gas purification unit (50) to the first storage compartment (A).

\* \* \* \* \*